United States Patent [19]

Higuchi et al.

[11] 4,246,399

[45] Jan. 20, 1981

[54] COMPLEXES OF DOXORUBICIN EXHIBITING ENHANCED STABILITY

[75] Inventors: Takeru Higuchi; Pramod M. Kotwal, both of Lawrence, Kans.

[73] Assignee: INTERx Research Corporation, Lawrence, Kans.

[21] Appl. No.: 779,847

[22] Filed: Mar. 21, 1977

[51] Int. Cl.$^3$ .................. C07H 15/24; A61K 31/71
[52] U.S. Cl. .................. 536/17 A; 536/121; 424/180
[58] Field of Search ............... 536/4, 17, 121, 17 R

[56] References Cited

U.S. PATENT DOCUMENTS

| | | | |
|---|---|---|---|
| 3,074,927 | 1/1963 | Saltman et al. | 536/121 |
| 3,590,028 | 6/1971 | Arcamone et al. | 536/17 |

OTHER PUBLICATIONS

Wilson et al., *Textbook of Organic Medicinal and Pharmaceutical Chemistry*, Seventh Edition, J. B. Lippincott Company, Philadelphia (1977), pp. 336, 337 and 339.

*Primary Examiner*—Johnnie R. Brown
*Attorney, Agent, or Firm*—Burns, Doane, Swecker & Mathis

[57] ABSTRACT

Complexes of the formula:

$$A \cdot X_n$$

wherein A represents doxorubicin; wherein X represents $Ca^{++}$, $Mg^{++}$, $Zn^{++}$, or $Ni^{++}$; and wherein n represents one or two having enhanced stability are disclosed.

The above-described compounds are inorganic complexes of a well-known and regulatory approved compound, doxorubicin, useful in the treatment of a variety of carcinomas. These complexes offer enhanced stability over doxorubicin per se.

5 Claims, No Drawings

COMPLEXES OF DOXORUBICIN EXHIBITING ENHANCED STABILITY

BACKGROUND OF THE INVENTION

1. Field of the Invention

The present invention is directed to a relatively new and regulatory approved antitumor agent, Adriamycin ® (Doxorubicin). More specifically, the present invention is directed to certain inorganic metallic complexes of Adriamycin ® which offer enhanced stability to the parent moiety, Adriamycin ®.

2. Description of the Prior Art

Adriamycin ® is a relatively new and regulatorily approved antitumor antibiotic which was isolated in 1967 from cultures of a mutant Streptomyces peucetius. Adriamycin ® has been used successfully to produce regression in a number of neoplastic conditions such as acute lymphoblastic leukemia, acute myeloblastic leukemia, Wilm's tumor, soft tissue osteogenic sarcoma, neuroblastoma, breast carcinoma, ovarian carcinoma, transitional cell bladder tumor, bronchiogenic lung carcinoma, thyroid carcinoma and lymphoma of both Hodgkin and non-Hodgkin types. A number of other solid tumors in the pediatric group have also shown some responsiveness to this recently developed drug. See, *PHYSICIAN'S DESK REFERENCE*, (1975), pgs. 550-551.

Because of Adriamycin's ® sole route of administration (intravenous infusion), hydrolytic cleavage of its "glycone" or sugar moiety is well pronounced such that stability of the overall molecule is diminished. As a result of such instability, prolonged therapeutic activity of the drug is diminished.

SUMMARY OF THE INVENTION

It is the primary object of the present invention to provide certain selected stable metallic complexes of Adriamycin ®.

It is another object of the present invention to provide a means to stabilize Adriamycin ® via complexation with certain selected metallic salts.

It is still another object of the present invention to provide stabilized complexes of Adriamycin ® which do not offer enhanced toxicity over the parent moiety, Adriamycin ®.

All the foregoing objects are achieved with certain selected metallic complexes of Adriamycin ® as described below:

$A.X_n$ wherein A represents Adriamycin ®; where X represents $Ca^{++}$, $Mg^{++}$, $Zn^{++}$ or $Ni^{++}$; and wherein n represents one or two having enhanced stability.

The above-described complexes are formed by contacting an aqueous solution of any pharmaceutically acceptable salt of $Ca^{++}$, $Mg^{++}$, $Ni^{++}$ or $Zn^{++}$ with Adriamycin ® and subsequently agitating the mixture over an extended period of time. In practice, the complexes of this invention are formed by contacting the Adriamycin ® in solution with an excess of the metallic salt employed. Since the Adriamycin ®, the metallic salt and the complex are in equilibrium, the excess of the complexing agent will favor the formation of the complex and will also tend to depress the solubility of the complex in the mother liquor. The actual ratio of complexing metallic salt to Adriamycin ® is depended upon the solvent employed, temperature and the nature of the complexing metallic salt. However, generally, the complexing metallic salt should be present in the range of 0.05 to 0.95 of its maximum solubility in the solvent employed.

Normally, the solvent of choice is water; however, suitable organic solvents such as methanol, ethanol, propanol, butanol, pentanol, acetone, etc. will also suffice. The complexing metallic salt solution and the Adriamycin ® should be contacted over a relatively long period of time under conditions of good agitation. Stirring periods upwards of 72 hours or longer give excellent results, though the exact period is not critical. The reaction proceeds at ambient pressure and room temperature. The individual complexes within the scope of this invention are then precipitated from the reaction mixture by simply seeding the reaction mixture with seed crystals of the desired product. Following the agitation period, the precipitated Adriamycin ® complex is filtered from the mother liquor and as much of the filtrate as possible is removed from the filter cake. The filtered complex is then dried by any conventional means and preferably in vacuo to remove any excess complexing metallic salt which has remained behind in the filter cake.

With reference to the expression "pharmaceutically acceptable salt" as previously used, denotes any nontoxic acid addition salt of $Ca^{++}$, $Mg^{++}$, $Ni^{++}$ or $Zn^{++}$, formed with nontoxic inorganic or organic acids. For example, the salts include those derived from inorganic acid such as hydrochloric, hydrobromic, sulfuric, sulfamic, phosphoric, nitric and the like; and the salts prepared from organic acid such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, toluenesulfonic and the like.

Without further elaboration, it is believed that one of ordinary skill in the art, can, using the preceding description, utilize the instant invention to its fullest extent. Consequently, the following preferred specific embodiments are, therefore, to be construed as merely illustrative and not limitative of the remainder of the specification and claims in any way whatsoever.

EXAMPLE I

MAGNESIUM COMPLEX OF ADRIAMYCIN ®

Adriamycin ® is contacted with an excess of an aqueous solution of magnesium chloride over a period of 24 hours with agitation. Subsequently, the resulting magnesium complex is precipitated in the manner previously described and then filtered in vacuo to yield a quantitative sample of the subject complex.

By following the procedure of Example I above, and simply introducing the appropriate generically and/or specifically described reactants and operating conditions previously noted, all remaining complexes of this invention are synthesized.

EXAMPLE II

STABILITY ANALYSIS

The magnesium complex of Example I was tested against Adriamycin ® per se for stability of the "glycone" moiety by standard High Pressure Liquid chromotography (HPLC) techniques. HPLC evaluation demonstrated the superior stability of the complex over Adriamycin ® per se. When repeating Example II and substituting the remaining complexes of this invention for the magnesium complex, substantially similar stability characteristics are observed.

All the complexes of the present invention are conveniently administered, per se, or in combination with any pharmaceutically acceptable inert parenteral carrier which include, without limitation, conventional isotonic sodium chloride vehicles, etc. Such can be readily ascertained by simply referring to the text entitled "REMINGTON'S PHARMACEUTICAL SCIENCES," Fourteenth Edition (1970).

The dose administered, whether a single dose or a daily dose, will, of course, vary with the needs of the individual being treated. However, the dosage administered is not subject to definite bounds, but it will usually be a safe and effective therapeutic amount, or the equivalent on a molar basis of the pharmacologically active form produced upon the metabolic release of the active drug (Adriamycin ®) to achieve its desired pharmacological or physiological effect. Normally, the medical dose for warm-blooded animals, including humans and primates, will, on an equivalent molar basis, mimic that of Adriamycin ®. See, *PHYSICIAN'S DESK REFERENCE*, noted supra.

From the foregoing description, one of ordinary skill in the art can easily ascertain the essential characteristics of this invention, and without departing from the spirit and scope thereof, can make various changes and/or modifications of the same to adapt it to various usages and conditions. As such, these changes and modifications are preferably, equitably and intended to be, within the full range of equivalence of the following claims.

What we claim is:

1. A complex of doxorubicin having the formula:

$$A \cdot X_n$$

wherein A represents doxorubicin having the structural formula:

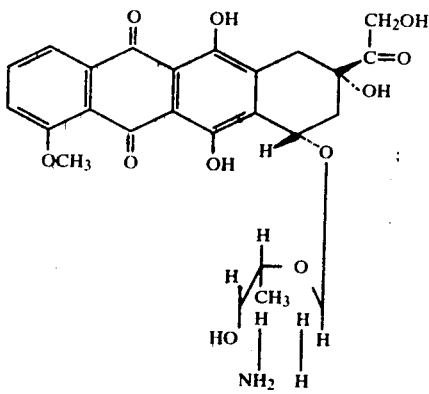

wherein X represents $Ca^{++}$, $Mg^{++}$, $Zn^{++}$ or $Ni^{++}$; and wherein n represents one or two.

2. The complex of claim 1, wherein X represents $Ca^{++}$.

3. The complex of claim 1, wherein X represents $Mg^{++}$.

4. The complex of claim 1, wherein X represents $Zn^{++}$.

5. The complex of claim 1, wherein X represents $Ni^{++}$.

* * * * *